US00PP16945P2

(12) United States Plant Patent
Zerr

(10) Patent No.: US PP16,945 P2
(45) Date of Patent: Aug. 8, 2006

(54) POINSETTIA PLANT NAMED 'FISHOLLY'

(50) Latin Name: *Euphorbia pulcherrima (Willd.)*
Varietal Denomination: Fisholly

(75) Inventor: Katharina Zerr, Hohr-Grenzhausen (DE)

(73) Assignee: Florfis AG, Binningen (CH)

( * ) Notice: Subject to any disclaimer, the term of this patent is extended or adjusted under 35 U.S.C. 154(b) by 81 days.

(21) Appl. No.: 11/071,956

(22) Filed: Mar. 4, 2005

(51) Int. Cl.
*A01H 5/00* (2006.01)

(52) U.S. Cl. ..... Plt./306
(58) Field of Classification Search ..... Plt./306
See application file for complete search history.

*Primary Examiner*—Kent Bell
*Assistant Examiner*—Annette H Para
(74) *Attorney, Agent, or Firm*—Jondle & Associates P.C.

(57) ABSTRACT

A Poinsettia cultivar particularly distinguished by its pink bract color with white margins, numerous relatively large cyathia, and compact to medium-sized round plant habit is disclosed.

1 Drawing Sheet

Figure 1:
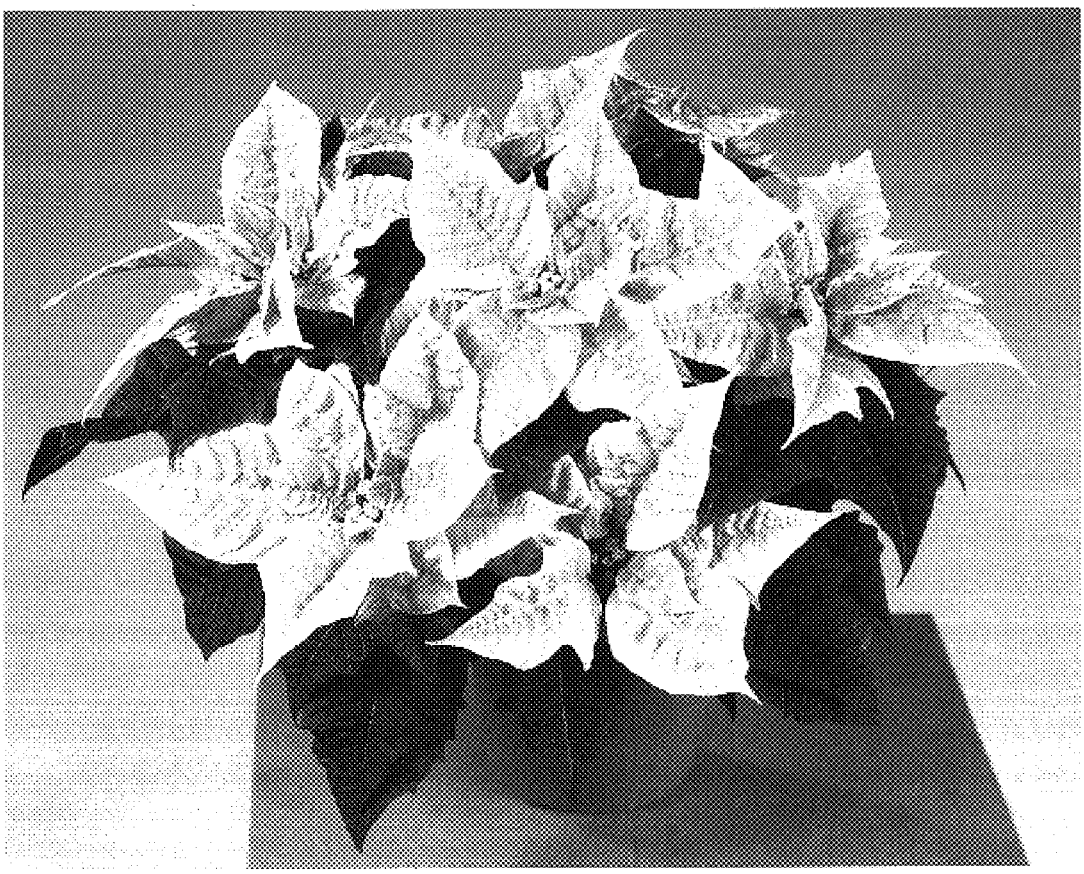

Genus and species: *Euphorbia pulcherrima* (Willd.).
Variety denomination: 'Fisholly'.

BACKGROUND OF THE NEW PLANT

The present invention relates to a new and distinct cultivar of poinsettia plant botanically known as *Euphorbia pulcherrima* (Willd.), and hereinafter referred to by the name 'Fisholly'. 'Fisholly' is the result of a naturally occurring mutation in the variety 'Fispic' (U.S. Plant Pat. No. 9,371). 'Fispic' is characterized by red-colored bracts, narrow leaves, and relatively compact plant habit.

In the fall of 1998, a pale pink-flowered plant was found among a crop of flowering 'Fispic' in a greenhouse in Hillscheid, Germany. The plant was propagated and its offspring were examined in the fall of 1999. The clone was kept among the breeding stock until 2002 when it was grown for further comparison. It appeared to have split into mainly uniform, pink-flowered plants and into pink- and cream-marbled-flowered plants. A plant of the pink- and cream-marbled- flowered type was propagated separately and was evaluated in 2003.

Horticultural examination of the plants starting in 2003 and continuing thereafter has confirmed that the combination of characteristics as herein disclosed for 'Fisholly' are firmly fixed and retained through successive generations of asexual reproduction.

The following traits have been repeatedly observed and are determined to be the basic characteristics of 'Fisholly' which in combination distinguish this Poinsettia as a new and distinct cultivar:

- pink bract color with white margins
- medium sized, funnel-shaped inflorescence, especially when grown as a miniature plant
- relatively many, big cyathia, often with several nectar cups each
- uniform, deep green foliage, ovate leaves with small pointed lobes
- compact to medium sized, round plant habit
- early to medium flowering response

DESCRIPTION OF PHOTOGRAPH

This new Poinsettia plant is illustrated by the accompanying photograph which shows the plant's form, foliage and flowers. The colors shown are as true as can be reasonably obtained by conventional photographic procedures.

FIG. 1 shows overall plant habit including foliage and flowers.

DESCRIPTION OF THE NEW CULTIVAR

'Fisholly' has not been observed under all possible environmental conditions. The phenotype may vary significantly with variations in environment such as temperature, light intensity, and day-length. The following observations, measurements and comparisons describe plants grown in Hillscheid, Germany under greenhouse conditions which approximate those generally used in commercial practice.

The plants described were grown in a greenhouse in Hillscheid, Germany from the summer to the fall of 2004. Rooted cuttings were planted in 14 cm pots on Jul. 22, 2004 and were pinched on August 6, which left 7–8 leaves remaining. Initially, the minimum temperature was 18° C. Beginning October 1, the temperature was lowered to a minimum temperature of 16 to 17° C. The plants initiated flowers under natural short-day conditions in fall. No black cloth was applied to the greenhouse to simulate short-day conditions. No growth regulator was applied.

Observations and measurements were mainly taken in early to mid-December, when the plants were in fully flower and 19–20 weeks old. In the following description, color references are made to The Royal Horticultural Society Colour Chart (R.H.S.). The color references were determined indoors in a north light.

DESCRIPTION OF THE NEW PLANT

Classification:
*Family.*—Euphorbiaceae.
*Botanical.*—*Euphorbia pulcherrima* (Willd. Ex Klotzsch).

Parentage: Mutation of Poinsettia cultivar 'Fispic' (U.S. Plant Pat. No. 9,371).

Growth:

*Time to produce a rooted cutting.*—20–24 days in a greenhouse at a temperature of 22–24° C.

*Blooming habit.*—Beginning under natural short-day conditions in fall: Botanically (cyathia open): About December 1. Commercially (bracts colored, marketable): Late November. Flowering response time: About 8–9 weeks. Keeping quality: Good lasting quality is maintained for about 4 weeks with no dropping of bracts.

Plant:

*Form.*—Shrub, self-branching.

*Growth habit.*—Compact to medium sized; pinched plants are bushy and round in shape.

*Height.*—26.0 cm as measured from soil line.

*Width.*—40 cm.

*Average number of branches.*—7.9.

*Length of branches.*—20–23 cm.

*Diameter of branches.*—0.4–0.6 cm.

*Average number of inflorescences.*—7.5.

Stems:

*Stem color.*—Middle part: RHS 143A (green). Upper part: RHS 143C (green). Internode length: 2.0 cm.

Leaves:

*Quantity.*—40–45 leaves per plant (5–6 leaves per branch).

*Shape.*—Ovate.

*Base.*—Rounded to obtuse.

*Apex.*—Acuminate.

*Lobes.*—Irregularly spread, small, pointed.

*Margin.*—Entire.

*Texture.*—Upper surface: Smooth and flat, only weakly veined. Lower surface: Flat and smooth, except for the slightly protruding midrib and finer side veins in a pinnate pattern.

*Vein color.*—Upper surface: RHS 143C (green). Lower surface: RHS 145B.

*Size.*—Length: 11.8 cm. Width: 8.9 cm.

*Color.*—Mature foliage: Upper surface: Near RHS 137A. Lower surface: RHS 137C. Immature foliage: Upper surface: RHS 143A. Lower surface: RHS 137D.

*Leaf petiole.*—Length: 6.0 cm. Diameter: 0.3 cm. Color: Upper surface: RHS 141D (green). Lower surface: RHS 145A.

*Aspect.*—Petioles and leaves are somewhat upward-directed.

Inflorescence:

*Whole inflorescence with surrounding bracts.*—Medium sized, weakly or distinctly funnel-shaped with the bracts somewhat upward-directed, middle is a tight cyme with relatively big cyathia.

*Diameter.*—26–27 cm.

*Height of inflorescence.*—4.5 cm.

Bracts:

*Number of bracts per inflorescence.*—14.

*Shape.*—Ovate.

*Base.*—Truncate to rounded.

*Apex.*—Acuminate.

*Lobes.*—Pointed.

*Size.*—Length: 13.5 cm. Width: 8.3 cm.

*Texture.*—Rugose or rippled to a relatively strong degree.

*Vein color.*—Upper surface: Corresponds closely to the bract color. Lower surface: RHS 149C (green).

*Bract color.*—Upper surface: RHS 51C (pink) with RHS 4D (cream white) margins.

*Petiole.*—Length.—1.7–2.7 cm. Color: Upper surface: Between RHS 150C and RHS 150D. Lower surface: RHS 149C.

Cyme:

*Cyme diameter.*—2.5–3.0 cm.

*Cyathia number.*—15 borne in a tight cluster.

*Cyathium.*—Shape: Ovate. Diameter: 0.6 cm. Length: 2.0 cm (peduncle and female flower). Color: RHS 144A (green); top is between RHS 150C and RHS 150D.

*Peduncle.*—Color: RHS 143C (green). Length: 0.3–0.4 cm.

*Nectar cups.*—Number: Usually two, sometimes 3–4 per cyathium. Size: 0.6 cm wide. Color: RHS 12A (yellow).

Reproductive organs:

*Stamens.*—Number: 1–5 in a cluster, usually not fertile, but abortive. Filaments: Length: 0.2–0.3 cm. Pollen: None observed.

*Pistil.*—Stigma shape: Trifurcate, 6-lobed. Style and stigma color: RHS 158D (cream white).

*Ovary.*—Color: RHS 143B (green). Shape: Obovate. Diameter: 0.3–0.4 cm. Length: 0.5–0.6 cm. Number of ovules: 3.

*Fruit/seed set.*—None observed.

Disease and insect resistance: No observations made.

COMPARISON WITH KNOWN CULTIVARS

The most similar cultivars in comparison to 'Fisholly' are the parental cultivar 'Fispic' (U.S. Plant Pat. No. 9,371) and the cultivar 'Fispue' (U.S. Plant Pat. No. 9,315). In comparison to 'Fispic', 'Fisholly' has a different bract color, variegated pink with white margins instead of deep orange-red, and somewhat shorter and relatively wider bracts and leaves. Furthermore, bracts of 'Fisholly' are more distinctly slanting upright forming a funnel-shaped inflorescence. Additionally, at the top end of every cyathium at least two nectar cups are formed, in contrast to usually only one nectar cup with 'Fispic'.

I claim:

1. A new and distinct cultivar of Poinsettia plant as shown and described herein.

* * * * *